United States Patent [19]

Meyer

[11] Patent Number: 4,480,101

[45] Date of Patent: Oct. 30, 1984

[54] FLUOROALKOXY-AMINOPYRIMIDINES

[75] Inventor: Willy Meyer, Riehen, Switzerland

[73] Assignee: Ciba-Geigy Corporation, Ardsley, N.Y.

[21] Appl. No.: 396,960

[22] Filed: Jul. 9, 1982

[30] Foreign Application Priority Data

| | | |
|---|---|---|
| Jul. 16, 1981 [CH] | Switzerland | 4667/81 |
| Aug. 6, 1981 [CH] | Switzerland | 5075/81 |
| Oct. 13, 1981 [CH] | Switzerland | 6541/81 |
| Jan. 11, 1982 [CH] | Switzerland | 124/82 |
| Apr. 8, 1982 [CH] | Switzerland | 2205/82 |
| Jun. 8, 1982 [CH] | Switzerland | 3527/82 |

[51] Int. Cl.$^3$ .................................. C07D 239/47
[52] U.S. Cl. .......................... 544/320; 544/213; 544/194
[58] Field of Search ......................... 544/320

[56] References Cited

U.S. PATENT DOCUMENTS 4,239,777 12/1980 Berkelhammer ............... 424/304

FOREIGN PATENT DOCUMENTS 2013424 10/1971 Fed. Rep. of Germany.

Primary Examiner—Robert Gerstl
Attorney, Agent, or Firm—Frederick H. Rabin

[57] ABSTRACT

There are described novel intermediates for herbicides of the sulfonylurea class, which have the general formula I

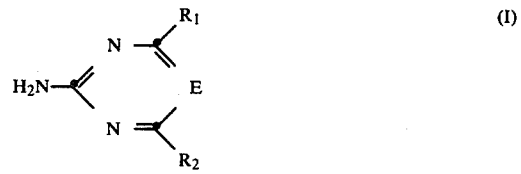

wherein
E is nitrogen or the methine group,
$R_1$ is halogen, $C_1$–$C_4$-alkyl, $C_1$–$C_4$-alkoxy, $C_1$–$C_4$-haloalkoxy, $C_1$–$C_4$-alkylthio, $C_1$–$C_4$-haloalkyl, —$NR_3R_4$ or alkoxyalkyl having at most 4 carbon atoms, and
$R_2$ is a group —G—$CF_2$—T, where G is oxygen or sulfur, T is hydrogen, —CHClF, —CHBrF, —$CHF_2$ or —CHF—$CF_3$, $R_3$ is hydrogen, methyl or ethyl, and $R_4$ is hydrogen, methyl, ethyl, methoxy, ethoxy or methoxymethyl, with the proviso that $R_1$ is not $C_1$–$C_4$-alkyl when simultaneously E is nitrogen and G is oxygen.

9 Claims, No Drawings

FLUOROALKOXY-AMINOPYRIMIDINES

The present invention relates to novel fluoroalkoxyaminopyrimidines and -triazines, to processes for obtaining them, and to their use in the synthesis of herbicides of the sulfonylurea class, as well as to N-fluoroalkoxypyrimidinyl- and -triazinylcarbamates produced as intermediates.

The fluoroalkoxy-aminopyrimidines and -triazines according to the invention have the general formula I

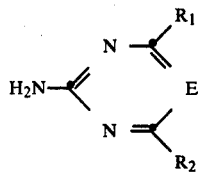

wherein

E is nitrogen or the methine group, $R_1$ is halogen, $C_1$-$C_4$-alkyl, $C_1$-$C_4$-alkoxy, $C_1$-$C_4$-haloalkoxy, $C_1$-$C_4$-alkylthio, $C_1$-$C_4$-haloalkyl, —$NR_3R_4$ or alkoxyalkyl having at most 4 carbon atoms, and $R_2$ is a group —G—$CF_2$—T, where G is oxygen or sulfur, T is hydrogen, —CHClF, —CHBrF, —$CHF_2$ or —CHF—$CF_3$, $R_3$ is hydrogen, methyl or ethyl, and $R_4$ is hydrogen, methyl, ethyl, methoxy, ethoxy or methoxymethyl, with the proviso that $R_1$ is not $C_1$-$C_4$-alkyl when simultaneously E is nitrogen and G is oxygen.

The novel fluoroalkoxy-aminopyrimidines and -triazines according to the invention are intermediates in the synthesis of various herbicides and plant-growth regulators of the sulfonylurea class. Sulfonylureas of this type are described in the Swiss Patent Application Nos. 4667/81-0, 5075/81-2, 6541/81-0, 124/82-4 and 2205/82-3.

Sulfonylureas having herbicidal activity have been known from the literature for a long time. They are for example described in the U.S. Pat. No. 4,127,405.

Haloalkoxytriazines are emphasised in the German Offenlegungsschrift No. 2,013,424 as being plant protective agents.

By halogen is meant within the scope of the above definition in general fluorine, chlorine, bromine or iodine. Fluorine or chlorine, especially however fluorine, is preferred.

Examples of alkyl are: methyl, ethyl, n-propyl, i-propyl or the isomeric butyl groups. Alkyl is a substituent itself or is a part of another substituent, such as for example: alkoxy, haloalkoxy, alkylthio, haloalkyl or alkoxyalkyl. Straight-chain alkyl chains, particularly however methyl and ethyl, are preferred.

The group of the compounds of the formula I falls into two large subgroups, which are preferred to an equal extent: these subgroups contain those compounds in which (a) $R_1$ is halogen, $C_1$-$C_4$-alkylthio, $C_1$-$C_4$-alkoxy, $C_1$-$C_4$-alkyl, $C_1$-$C_4$-haloalkoxy, $C_1$-$C_4$-haloalkyl or alkoxyalkyl having at most 4 carbon atoms; and those compounds in which (b) $R_1$ is the group —$NR_3R_4$, in which $R_3$ is hydrogen, methyl or ethyl, and $R_4$ is hydrogen, methyl, ethyl, methoxy, ethoxy or methoxymethyl.

To be mentioned as further preferred subgroups are: compounds of the formula I in which (c) $R_2$ is 1,1,2,2-tetrafluoroethoxy, and in which (d) $R_2$ is —G—$CHF_2$, wherein -G is oxygen or sulfur.

A particularly preferred subgroup of compounds of the (c) group is formed by the compounds in which $R_1$ is fluorine, chlorine, methyl, ethyl, methoxy, ethoxy, difluoromethoxy, trifluoromethyl, fluoromethyl, methoxymethyl or —$NR_3R_4$, wherein $R_3$ is hydrogen or methyl, and $R_4$ is methyl or ethyl.

An especially preferred subgroup of compounds of the group (d) is made up of compounds in which E is the methine group, G is oxygen, $R_1$ is fluorine, chlorine, methyl, ethyl, methoxy, ethoxy, difluoromethoxy, trifluoromethyl, fluoromethyl, methoxymethyl or —$NR_3R_4$, wherein $R_3$ is hydrogen or methyl, and $R_4$ is methyl or ethyl.

Among these compounds, a further group to be emphasised comprises the compounds in which $R_1$ is methyl, ethyl, methoxy, ethoxy, difluoromethoxy, dimethylamino or ethylmethylamino.

The compounds of the formula I are produced by reacting an amino compound of the formula II

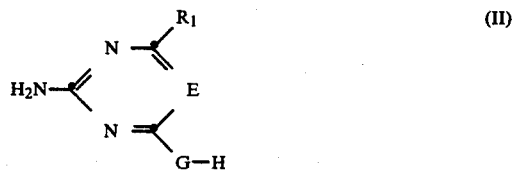

wherein E and $R_1$ have the meanings defined under the formula I, and G is oxygen or sulfur, in the presence of a base, with difluorochloromethane, tetrafluoroethylene, trifluorochloroethylene, trifluorobromoethylene, hexafluoropropylene or difluorobromomethane.

The process for producing the compounds of the formula I is advantageously performed in an inert polar solvent or solvent mixture. Suitable solvents are ethers, such as dioxane, tetrahydrofuran, ethylene glycol dimethyl ether, or diethylene glycol dimethyl ether; alcohols, such as methanol, ethanol or isopropanol; ketones, such as acetone or ethyl methyl ketone; dimethylformamide; acetonitrile or dimethyl sulfoxide. Bases which are particularly suitable are: sodium and calcium hydride, potassium and sodium hydroxide and potassium and sodium carbonate. The base can in suitable cases be added in the form of an aqueous solution.

When gaseous fluorinated hydrocarbons are used as starting materials for producing the compounds of the formula I, it can be of advantage to perform the reaction under elevated pressure. Pressures of up to 100 bar, preferably up to 20 bar, can be used for the process.

The reaction temperatures are in general between 0° and 120° C., preferably between 20° and 100° C.

In some cases it is advantageous to carry out the reaction in the presence of a phase-transfer catalyst, for example a quaternary ammonium compound or a crown ether.

The fluoroalkoxy-aminopyrimidines and -triazines according to the invention are converted into the herbicidal sulfonylureas, using the procedure given in the Swiss Patent Application Nos. 4667/81-0, 5075/81-2, 6541/81-0, 124/82-4 and 2205/82-3, (a) by reacting the fluoroalkoxy-aminopyrimidine or -triazine of the formula I, optionally in the presence of a base, with a sulfonylisocyanate or -isothiocyanate of the formula III

$$X-SO_2-N=C=Z \quad (III)$$

wherein X is an aromatic radical included in the stated patent applications, and Z is oxygen or sulfur; or (b) by reacting the fluoroalkoxy-aminopyrimidine or -triazine of the formula I with a carbamate of the formula IV

$$X-SO_2-NH-\overset{\overset{Z}{\|}}{C}-O-C_6H_5 \quad (IV)$$

wherein X is an aromatic radical included in the stated patent applications and Z is oxygen or sulfur; or (c) by firstly converting the fluoroalkoxy-aminopyrimidine or -triazine of the formula I into an isocyanate or isothiocyanate of the formula V

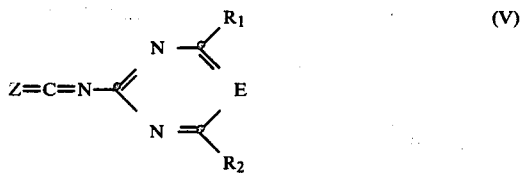

(V)

wherein E, $R_1$ and $R_2$ have the meanings given under the formula I, and Z is oxygen or sulfur, and then reacting the product obtained, optionally in the presence of a base, with a sulfonamide of the formula VI $$X-SO_2-NH_2 \quad (VI)$$

wherein X is an aromatic radical included in the stated patent applications; or (d) by firstly converting the fluoroalkoxy-aminopyrimidine or -triazine of the formula I into an N-fluoroalkoxy-pyrimidinyl- or -triazinylcarbamate of the formula VII

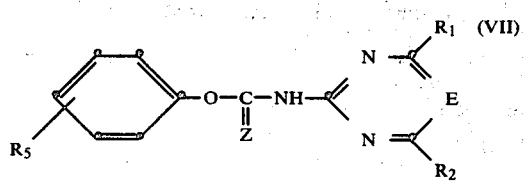

(VII)

wherein E, $R_1$ and $R_2$ have the meanings defined under the formula I, Z is oxygen or sulfur, and $R_5$ is a substituent from the series comprising hydrogen, halogen, nitro or $C_1$-$C_3$-alkyl, and then reacting the product obtained, in the presence of a base, with a sulfonamide of the formula VI given above.

The use of the compounds of the formula I according to the invention for the synthesis of herbicides of the sulfonylurea class likewise forms subject matter of the present invention.

The starting materials of the formulae III, IV and VI are known, described in the patent applications mentioned, or can be produced by known methods.

Isocyanates and isothiocyanates of the formula V are novel, and can be produced, by processes analogous to known processes, from the compounds of the formula I according to the invention. Similar reactions are described in "Neuere Methoden der präparativen organischen Chemie", Vol. VI, 211-223, Verlag Chemie, Weinheim 1970, and in Arch. Pharm. 299, 174 (1966).

N-Fluoroalkoxypyrimidinyl- and -triazinylcarbamates of the formula VII are novel, and have been specially produced for the conversion of the compounds of the formula I, under mild reaction conditions, into the herbicidal sulfonylureas of the stated patent applications. They therefore likewise constitute a further aspect of the present invention.

The compounds of the formula VII are produced by reacting carbonic acid derivatives of the formula VIII

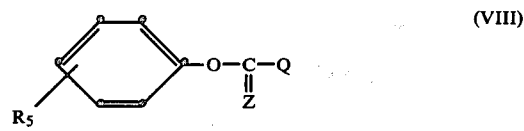

(VIII)

wherein Z and $R_5$ are as defined under the formula VII, and Q is chlorine or bromine, or phenoxy substituted by $R_5$, optionally in the presence of a base, with an amine of the formula I.

The process for producing compounds of the formula VII is advantageously performed in an inert aprotic solvent at temperatures of between 20° and 120° C. Suitable solvents are: ethers, such as diethyl ether, dioxane, tetrahydrofuran, ethylene glycol dimethyl ether or diethylene glycol dimethyl ether; ketones, such as acetone, ethyl methyl ketone or cyclohexanone; hydrocarbons, such as benzene, toluene, xylene or cyclohexane; chlorinated hydrocarbons, such as methylene chloride, chloroform or carbon tetrachloride; dimethylformamide; N-methylpyrrolidinone; acetonitrile or dimethyl sulfoxide. Suitable bases are for example in particular: tertiary amines, such as triethylamine, quinuclidine, quinoline, pyridine, trimethylamine, 4-dimethylaminopyridine, carbonates, such as sodium or potassium carbonate, or hydrides, such as sodium or calcium hydride. The bases are advantageously used in excess.

The amine of the formula I can in certain cases be used in excess, and thus serve as a base in the reaction.

The following Examples serve to further illustrate the present invention.

EXAMPLE 1

2-Amino-4-difluoromethylthio-6-methoxy-pyrimidine (a) 16.0 g of 2-amino-4-chloro-6-methoxy-pyrimidine are added portionwise to a solution of 8.0 g of thiourea in 85 ml of 15% hydrochloric acid. The formed brown solution is stirred for 24 hours at 20° to 25° C., and 140 ml of 25% sodium hydroxide solution are then added; the reaction mixture is subsequently filtered, and again acidified with hydrochloric acid, whereupon 10.7 g of 2-amino-4-mercapto-6-methoxy-pyrimidine precipitate; decomposition: 255° C., sinters from 188° C.

(b) Gaseous difluorochloromethane is introduced for 1½ hours at 60° to 65° C. into a suspension of 7.8 g of 2-amino-4-mercapto-6-methoxy-pyrimidine and 30 ml of concentrated sodium hydroxide solution in 100 ml of dioxane. By the addition of water, extraction with ethyl acetate, concentration of the organic phase by evaporation and crystallisation from methanol at −78° C., there are obtained 6.4 g of 2-amino-4-difluoromethylthio-6-methoxy-pyrimidine, m.p. 83° to 84° C. (compound No. 1.13).

EXAMPLE 2

2-Amino-4-difluoromethoxy-6-methyl-pyrimidine

Gaseous difluorochloromethane is introduced, over a period of 12 hours at a temperature of 70° to 75° C., into a solution of 62.5 g of 2-amino-4-hydroxy-6-methyl-pyrimidine in 500 ml of water, 100 ml of 40% sodium hydroxide solution and 100 ml of dioxane. There are added during this time, in each case at intervals of 1 hour and in equal portions, a total of 160 g of solid sodium hydroxide. The organic phase is separated, and concentrated to about 1/10 of its volume; the residue is poured into water, and the solid substance which has precipitated is removed. The yield is 39.9 g of 2-amino-4-difluoromethoxy-6-methyl-pyrimidine, m.p. 136° to 137° C. (compound No. 1.1).

EXAMPLE 3

2-Amino-4,6-bis-(difluoromethoxy)-pyrimidine

In a manner analogous to that of Example 2, there are obtained from 63.5 g of 2-amino-4,6-dihydroxy-pyrimidine, by the introduction during 6 hours of 105 g of difluoromethane, 7.3 g of 2-amino-4,6-bis-(difluoromethoxy)pyrimidine, m.p. 63° to 65° C. (compound No. 1.11).

EXAMPLE 4

2-Amino-4-difluoromethylthio-6-methoxy-1,3,5-triazine 10.0 g of gaseous difluorochloromethane are introduced, during a period of 90 minutes at a temperature of 70° to 75° C., into a suspension of 5.0 g of 2-amino-4-mercapto-6-methoxy-1,3,5-triazine and 4.8 g of potassium carbonate in 100 ml of dimethylformamide. The reaction mixture is concentrated by evaporation, the residue is stirred up with water, and the solid precipitate is separated. The yield is 1.6 g of 2-amino-4-difluoromethylthio-6-methoxy-1,3,5-triazine, m.p. 146° to 150° C. (compound No. 1.14).

EXAMPLE 5

2-Amino-4-chloro-6-difluoromethoxy-pyrimidine

A suspension of 16.4 g of 2-amino-4,6-dichloropyrimidine in 100 ml of 40% sodium hydroxide solution is stirred for 1 hour at a temperature of 95° to 100° C. After the addition of 200 ml of dioxane, there are added at a temperature of 70° to 75° C., within 1 hour, 20 g of gaseous difluoromethane. The organic phase is separated, and concentrated to about 1/5 of its volume; it is then poured into water and the solid precipitate is removed. The yield is 6 g of 2-amino-4-chloro-6-difluoromethoxy-pyrimidine, m.p. 118° to 119° C. (compound No. 1.7).

EXAMPLE 6

2-Amino-4-difluoromethoxy-6-methoxy-pyrimidine 19.2 g of 2-amino-4,6-dimethoxy-pyrimidine hydrochloride are heated at 150° C. for 2 hours, in the course of which methyl chloride is removed and 2-amino-4-hydroxy-6-methoxy-pyrimidine is formed. After the addition of 80 ml of 40% sodium hydroxide solution and 100 ml of dioxane, there are introduced at 70° to 75° C., during 45 minutes, 22 g of difluorochloromethane. The organic phase is then separated, concentrated to about 1/5 of its volume and poured into water, and the solid precipitate is removed. The yield is 2.4 g of 2-amino-4-difluoromethoxy-6-methoxy-pyrimidine, m.p. 106° to 107° C. (compound No. 1.7).

EXAMPLE 7

2-Amino-4-methyl-6-[1,1,2-trifluoro-2-chloro-ethoxy]-pyrimidine 25 g of 2-amino-4-hydroxy-6-methyl-pyrimidine, 25.6 g of chlorotrifluoroethylene, 13.8 g of potassium hydroxide and 200 ml of dimethylformamide are stirred together for 8 hours at 60° C. in an autoclave. The reaction mixture is diluted with water, extracted with ethyl acetate and concentrated by evaporation to obtain a dark oil. After the addition of a small amount of methylene chloride and separation of the formed crystalline precipitate, the yield is 8.7 g of 2-amino-4-methyl-6-(1,1,2-trifluoro-2-chloro-ethoxy)-pyrimidine, m.p. 73° to 74° C. (compound No. 1.42).

EXAMPLE 8

N-(2-Difluoromethoxyphenyl-sulfonyl)-N'-(4-difluoromethoxy-6-methyl-pyrimidin-2-yl)-urea A mixture of 2.5 g of 2-difluoromethoxyphenyl-sulfonylisocyanate, 1.75 g of 2-amino-4-difluoromethoxy-6-methylpyrimidine and 30 ml of absolute dioxane is stirred at a temperature of 70° to 75° C. for 2 hours. The solution is concentrated by evaporation, and the residue is then crystallised from ether to obtain 4.0 g of N-(2-difluoromethoxyphenyl-sulfonyl)-N'-(4-difluoromethoxy-6-methylpyrimidin-2-yl)-urea, m.p. 163° to 164° C.

EXAMPLE 9

N-(2-Methoxycarbonylphenyl-sulfonyl-N'-[(4,6-bis-(difluoromethoxy)-pyrimidin-2-yl]-urea In a manner analogous to that of Example 8, there are obtained, from 3.62 g of 2-methoxycarbonyl-sulfonylisocyanate and 2.63 g of 2-amino-4,6-bis-(difluoromethoxy)-pyrimidine in 50 ml of dioxane, 3.9 g of N-(2-methoxycarbonylphenyl-sulfonyl)-N'-[4,6-bis-(difluoromethoxy)pyrimidin-2-yl]-urea, m.p. 186° to 188° C.

EXAMPLE 10

N-[2-(2-Ethoxy-ethoxy)-phenyl-sulfonyl]-N'-(4-difluoromethoxy-6-methyl-pyrimidin-2-yl)-urea (a) To a solution of 9.0 g of 2-amino-4-difluoromethoxy-6-methyl-pyrimidine in 30 ml of absolute tetrahydrofuran are added successively 3.9 g of chloroformic acid-phenyl ester and 0.05 g of 4-dimethylamino-pyridine. After the solution has been stirred at 20° to 25° C. for 24 hours, the reaction mixture is diluted with 250 ml of ethyl acetate, and the occurring precipitate is separated. There are thus obtained 3.1 g of 2-amino-4-difluoromethoxy-6-methyl-pyrimidine hydrochloride, m.p. 204° to 205° C. (decomposition). In order to remove the residual starting material, the filtrate is eluted through an acid with ion-exchanger I ®(MERCK), dried over sodium sulfate and concentrated by evaporation to thus obtain as crude product, in the form of a viscous oil, 4.0 g of 2-phenoxycarbonylamino-4-difluoromethoxy-6-methyl-pyrimidine (compound No. 2.28), which melts at 56° to 58° C. after crystallisation;

$^1$H-NMR (CDCl$_3$)=2.5(s,CH$_3$), 6.45(s,1H), 7.0–7.5(5H), 7.56(t, J=70 Hz, CHF$_2$) and 9.0(NH ppm).

(b) A solution of 3.5 g of 2-phenoxycarbonylamino-4-difluoromethoxy-6-methyl-pyrimidine (crude product) and 2.9 g of 2-(ethoxy-ethoxy)-benzenesulfonamide in 100 ml of absolute acetonitrile is decomposed with 1.8 g of 1,5-diazabicyclo[5.4.0]undec-5-ene; it is then stirred for 1 hour at 20° to 25° C., diluted with 500 ml of water and acidified with hydrochloric acid. The precipitated oil is taken up with 200 ml of ethyl acetate, dried over sodium sulfate and concentrated by evaporation. Crystallisation of the oily residue from diethyl ether and acetone yields, as colourless crystals, N-[2-(2-ethoxy-ethoxy)-phenyl-sulfonyl]-N'-(4-difluoromethoxy-6-methyl-pyrimidin-2-yl)-urea, m.p. 90° to 95° C. (decomposition); yield 2.7 g.

There are obtained in an analogous manner the compounds of the formula I which are listed in the following Tables, and the intermediates produced therefrom for the synthesis of sulfonylurea herbicides.

TABLE 1

| Comp. No. | $R_1$ | $R_2$ | E | m.p. [°C.] |
|---|---|---|---|---|
| 1.1 | —$CH_3$ | —$OCHF_2$ | CH | 136–137° |
| 1.2 | —$CH_2F$ | —$OCHF_2$ | CH | |
| 1.3 | —$CH_2CH_3$ | —$OCHF_2$ | CH | 76–77° |
| 1.4 | —$CH_2OCH_3$ | —$OCHF_2$ | CH | |
| 1.5 | —$CF_3$ | —$OCHF_2$ | CH | 95–98° |
| 1.6 | —Cl | —$OCHF_2$ | CH | 118–119° |
| 1.7 | —$OCH_3$ | —$OCHF_2$ | CH | 106–107° |
| 1.8 | —$OCH_2CF_3$ | —$OCHF_2$ | CH | |
| 1.9 | —$OCH_2CH_3$ | —$OCHF_2$ | CH | |
| 1.10 | —$OCH(CH_3)_2$ | —$OCHF_2$ | CH | |
| 1.11 | —$OCHF_2$ | —$OCHF_2$ | CH | 63–65° |
| 1.12 | —$SCH_3$ | —$OCHF_2$ | CH | |
| 1.13 | —$OCH_3$ | —$SCHF_2$ | CH | 83–84° |
| 1.14 | —$OCH_3$ | —$SCHF_2$ | N | 146–150° |
| 1.15 | —$CH_3$ | —$SCHF_2$ | N | |
| 1.16 | —$CH_3$ | —$SCHF_2$ | CH | |
| 1.17 | —$OCH_3$ | —$OCHF_2$ | N | |
| 1.18 | —$N(CH_3)_2$ | —$OCHF_2$ | CH | 99–100° |
| 1.19 | —$N(CH_3)_2$ | —$SCHF_2$ | CH | |
| 1.20 | —$CH_3$ | —O—$CF_2$—$CHF_2$ | CH | 102–103° |
| 1.21 | —$CH_3$ | —O—$CF_2$—CHFBr | CH | |
| 1.22 | —$CH_3$ | —O—$CF_2$—CHF—$CF_3$ | CH | |
| 1.23 | —$OCH_3$ | —O—$CF_2$—CHFCl | CH | 56–57° |
| 1.24 | —$OCH_3$ | —O—$CF_2$—$CHF_2$ | CH | |
| 1.25 | —$OCH_3$ | —O—$CF_2$—CHF—$CF_3$ | CH | |
| 1.26 | —$C_2H_5$ | —O—$CF_2$—$CHF_2$ | CH | |
| 1.27 | —$C_2H_5$ | —O—$CF_2$—CHFCl | CH | |
| 1.28 | —Cl | —O—$CF_2$—$CHF_2$ | CH | |
| 1.29 | —Cl | —O—$CF_2$—CHFCl | CH | 59–60° |
| 1.30 | —$SCH_3$ | —O—$CF_2$—$CHF_2$ | N | |
| 1.31 | —$SCH_3$ | —O—$CF_2$—CHFCl | N | |
| 1.32 | —$SCH_3$ | —O—$CF_2$—CHFBr | N | |
| 1.33 | —$SCH_3$ | —O—$CF_2$—CHF—$CF_3$ | N | |
| 1.34 | —$OCH_3$ | —O—$CF_2$—$CHF_2$ | N | |
| 1.35 | —$OCH_3$ | —O—$CF_2$—CHFCl | N | |
| 1.36 | —$OCH_3$ | —O—$CF_2$—CHFBr | N | |
| 1.37 | —$OCH_3$ | —O—$CF_2$—CHF—$CF_3$ | N | |
| 1.38 | —$OC_2H_5$ | —O—$CF_2$—$CHF_2$ | N | |
| 1.39 | —$OCH_2CF_3$ | —O—$CF_2$—$CHF_2$ | N | |
| 1.40 | —$SCH_3$ | —O—$CF_2$—CHFCl | CH | |
| 1.41 | —$SCH_3$ | —O—$CF_2$—$CHF_2$ | CH | |
| 1.42 | —$CH_3$ | —O—$CF_2$—CHFCl | CH | 73–74° |
| 1.43 | —$N(CH_3)_2$ | —$SCHF_2$ | N | |
| 1.44 | —$NHCH_3$ | —$OCHF_2$ | CH | |
| 1.45 | —$N(CH_3)OCH_3$ | —$OCHF_2$ | CH | |
| 1.46 | —$N(CH_3)C_2H_5$ | —$OCHF_2$ | CH | |
| 1.47 | —$N(CH_3)_2$ | —$OCF_2$—$CHF_2$ | CH | |

TABLE 2

| Comp. No. | $R_1$ | $R_2$ | $R_5$ | E | Physical data |
|---|---|---|---|---|---|
| 2.1 | —$C_2H_5$ | —$OCHF_2$ | H | CH | |

TABLE 2-continued

![structure with R5-phenyl-O-CO-NH-pyrimidine bearing R1, R2, E]

| Comp. No. | R₁ | R₂ | R₅ | E | Physical data |
|---|---|---|---|---|---|
| 2.2 | —OCH₃ | —OCHF₂ | H | CH | |
| 2.3 | —OCHF₂ | —OCHF₂ | H | CH | |
| 2.4 | —Cl | —OCHF₂ | H | CH | |
| 2.5 | —OCH₃ | —SCHF₂ | H | CH | |
| 2.6 | —CH₃ | —OCF₂—CHF₂ | H | CH | |
| 2.7 | —OCH₃ | —OCF₂—CHF₂ | H | CH | |
| 2.8 | —OCH₂—CF₃ | —OCF₂—CHF₂ | H | CH | |
| 2.9 | —Cl | —OCF₂—CHF₂ | H | CH | |
| 2.10 | —N(CH₃)₂ | —OCF₂—CHF₂ | H | CH | |
| 2.11 | —OCH₃ | —OCF₂—CHF₂ | H | N | |
| 2.12 | —CH₃ | —OCF₂—CHClF | H | N | |
| 2.13 | —CH₃ | —OCF₂—CHF₂ | H | N | |
| 2.14 | —OCH₃ | —OCF₂—OHClF | H | CH | |
| 2.15 | —C₂H₅ | —OCF₂—CHF₂ | H | CH | |
| 2.16 | —CF₃ | —OCHF₂ | H | CH | |
| 2.17 | —CH₂F | —OCHF₂ | H | CH | |
| 2.18 | —CF₃ | —OCF₂—CHF₂ | H | CH | |
| 2.19 | —OCH₂—CF₃ | —OCHF₂ | H | CH | |
| 2.20 | —CH₃ | —OCF₂—CHClF | H | CH | |
| 2.21 | —Cl | —OCF₂—CHClF | H | CH | |
| 2.22 | —CH₃ | —OCHF₂ | 4-Cl | CH | |
| 2.23 | —OCH₃ | —OCHF₂ | 4-Cl | CH | |
| 2.24 | —Cl | —OCHF₂ | 4-Cl | CH | |
| 2.25 | —CF | —OCHF₂ | 4-Cl | CH | |
| 2.26 | —CH₃ | —OCHF₂ | 4-CH₃ | CH | |
| 2.27 | —CH₃ | —OCHF₂ | 4-NO₂ | CH | |
| 2.28 | —CH₃ | —OCHF₂ | H | CH | m.p. 56–58° C. |

What is claimed is:

1. A fluoroalkoxy-aminopyrimidine of the general formula I

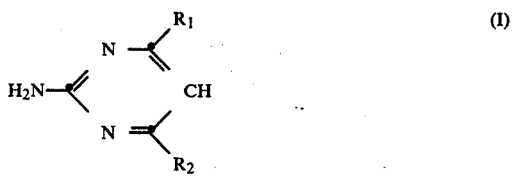

wherein
R₁ is halogen, $C_1$–$C_4$-alkyl, $C_1$–$C_4$-alkoxy, $C_1$–$C_4$-haloalkoxy, $C_1$–$C_4$-alkylthio, $C_1$–$C_4$-haloalkyl, —NR₃R₄ or alkoxy alkyl having at most 4 carbon atoms, and
R₂ is a group —G—CF₂—T, where G is oxygen or sulfur, T is hydrogen, —CHClF, —CHBrF, —CHF₂ or —CHF—CF₃, R₃ is hydrogen, methyl or ethyl, and R₄ is hydrogen, methyl, ethyl, methoxy, ethoxy or methoxymethyl, with the proviso that R₁ is not $C_1$–$C_4$-alkyl when simultaneously E is nitrogen and G is oxygen.

2. A compound according to claim 1, wherein R₁ is halogen, $C_1$–$C_4$-alkyl, $C_1$–$C_4$-alkoxy, $C_1$–$C_4$-haloalkoxy, $C_1$–$C_4$-alkylthio, $C_1$–$C_4$-haloalkyl or alkoxyalkyl having at most 4 carbon atoms.

3. A compound according to claim 1, wherein R₁ is the group —NR₃R₄, in which R₃ is hydrogen, methyl or ethyl, and R₄ is hydrogen, methyl, ethyl, methoxy, ethoxy or methoxymethyl.

4. A compound according to claim 1, wherein R₂ is 1,1,2,2-tetrafluoroethoxy.

5. A compound according to claim 1, wherein R₂ is —G—CHF₂, wherein G is oxygen or sulfur.

6. A compound according to claim 4, wherein R₁ is fluorine, chlorine, methyl, ethyl, methoxy, ethoxy, difluoromethoxy, trifluoromethyl, fluoromethyl, methoxymethyl or —NR₃R₄, wherein R₃ is hydrogen or methyl. and R₄ is methyl or ethyl.

7. A compound according to claim 5, wherein G is oxygen, R₁ is fluorine, chlorine, methyl, ethyl, methoxy, ethoxy, difluoromethoxy, trifluoromethyl, fluoromethyl, methoxymethyl or —NR₃R₄, wherein R₃ is hydrogen or methyl, and R₄ is methyl or ethyl.

8. A compound according to claim 7, wherein R₁ is methyl, ethyl, methoxy, ethoxy, difluoromethoxy, dimethylamino or ethylmethylamino.

9. The compound according to claim 8 which is 2-amino-4-difluoromethoxy-6-methylpyrimidine.

* * * * *